(12) United States Patent
Gautron et al.

(10) Patent No.: US 8,842,275 B2
(45) Date of Patent: *Sep. 23, 2014

(54) METHOD FOR ESTIMATING LIGHT SCATTERING (75) Inventors: Pascal Gautron, Cesson Sevigne Cedex (FR); Jean-Eudes Marvie, Cesson Sevigne Cedex (FR); Cyril Delalandre, Cesson Sevigne Cedex (FR)

(73) Assignee: Thomson Licensing (FR)

( * ) Notice: Subject to any disclaimer, the term of this patent is extended or adjusted under 35 U.S.C. 154(b) by 244 days.

This patent is subject to a terminal disclaimer.

(21) Appl. No.: 13/508,361

(22) PCT Filed: Nov. 9, 2010

(86) PCT No.: PCT/EP2010/067108
§ 371 (c)(1),
(2), (4) Date: May 5, 2012

(87) PCT Pub. No.: WO2011/058007
PCT Pub. Date: May 19, 2011

(65) Prior Publication Data
US 2012/0218549 A1  Aug. 30, 2012

(30) Foreign Application Priority Data
Nov. 16, 2009  (FR) ..................... 09 58071

(51) Int. Cl.
*G01N 21/00* (2006.01)
*G01N 15/02* (2006.01)
*G06T 15/50* (2011.01)
*G01N 15/14* (2006.01)

(52) U.S. Cl.
CPC .......... *G06T 15/506* (2013.01); *G01N 15/0205* (2013.01); *G01N 15/1459* (2013.01)
USPC ................ 356/337; 356/341; 703/2; 345/426

(58) Field of Classification Search
CPC .......... G01N 15/0205; G01N 15/1459; G01N 21/29; G01N 2015/1486; G01N 21/53
USPC ..................... 356/337, 341; 345/426
See application file for complete search history.

(56) References Cited

U.S. PATENT DOCUMENTS 7,940,268 B2 * 5/2011 Zhou et al. ..................... 345/426
7,940,269 B2 * 5/2011 Zhou et al. ..................... 345/426

(Continued)

FOREIGN PATENT DOCUMENTS

WO  WO-2009003143  12/2008

OTHER PUBLICATIONS

Schonefeld, "Spherical Harmonics," Jul. 1, 2005, retrieved from the internet, pp. 1-25.

(Continued)

*Primary Examiner* — Tarifur Chowdhury
*Assistant Examiner* — Isiaka Akanbi
(74) *Attorney, Agent, or Firm* — Jack Schwartz and Associates, PLLC (57) ABSTRACT

The invention relates to a method for estimating the quantity of light scattered by a heterogeneous participating media, the light being transmitted by a light environment comprising a plurality of light sources. In order to improve the display while minimising the required calculation time, the method comprises steps for:
  estimation of first projection coefficients in an orthonormal basis of spherical functions, said first projection coefficients being representative of the reduction of light intensity in a point of said media, said estimation of first projection coefficients being carried out for each point of a first set of points of said media, and
  estimation of the quantity of light scattered by said media, according to at least one scattering direction of the light, using said first estimated projection coefficients.

10 Claims, 7 Drawing Sheets

(56) References Cited

U.S. PATENT DOCUMENTS

2013/0100135 A1* 4/2013 Delalandre et al. ............ 345/426
2013/0346041 A1* 12/2013 Gautron et al. .................. 703/2

OTHER PUBLICATIONS

Tokuyoshi et al., "A First Rendering Method for a Scene with Participating Media of Anisotropic Scattering Property," Computer Graphics International 2006, Stony Brook, NY, Jun. 22-24, 2005, pp. 227-233.
Cerezo et al., "A Survey on Participating Media Rendering Techniques," Journal of Computer Graphics, Springer, Berlin, DE, vol. 21, No. 5, Jun. 1, 2005, pp. 303-326.
Jensen, "Realistic Image Synthesis Using Photo Mapping," A. K. Peters Ltd., Dec. 31, 2001, pp. 113-132.
Search Report Dated Jun. 9, 2011.

* cited by examiner

METHOD FOR ESTIMATING LIGHT SCATTERING

This application claims the benefit, under 35, U.S.C. §365, of International Application PCT/EP2010/067108, filed Nov. 09, 2010, which was published in accordance with PCT Article 21(2) on May 19, 2011, in French and which claims the benefit of French patent application No. 0958071, filed Nov. 16, 2009

1. DOMAIN OF THE INVENTIONS

The invention relates to the domain of synthesis image composition and more specifically to the domain of light scattering simulation in a heterogeneous participating media. The invention is also understood in the context of special effects for a live composition.

2. PRIOR ART

According to the prior art, different methods exist for simulating the scattering of light in participating media such as for example fog, smoke, dust or clouds. Participating media correspond to media composed of particles in suspension that interact with the light modifying particularly the trajectory and intensity.

Participating media can be broken down into two groups, namely homogenous media such as water and heterogeneous media, such as smoke or clouds. In the case of homogenous participating media, it is possible to calculate analytically the attenuation of the light transmitted by a light source. In fact, due to their homogenous nature, these media have parameters such as the light absorption coefficient or the light scattering coefficient that are constant at any point of the media. Conversely, the light absorption and scattering properties vary from one point to another in a heterogeneous participating media. The calculations required to simulate the scattering of light in such a heterogeneous media are then very costly and it is thus not possible to calculate analytically and live the quantity of light scattered by a heterogeneous participating media. In addition, the media not being scattered (that is to say the scattering of the media being anisotropic), the quantity of light scattered by the media also varies according to the scattering direction of the light, that is to say the direction in which a person views the media. Calculations estimating the quantity of light scattered must then be reiterated for each observation direction of the media by a person hi order to obtain a realist display of the media.

To produce the live display of heterogeneous participating media, some methods perform the pre-calculation of some parameters representative of the heterogeneous participating media. Though these methods are perfectly adapted for a studio use in post-production for example and provide a good quality display, these methods are not adapted in the context of live interactive conception and composition of a heterogeneous participating media. Such a method is described for example in the patent application WO2009/003143, filed by Microsoft Corporation and published on 31, Dec. 2008. The purpose of the application WO2009/003143, is a live display application for a heterogeneous media and describes a solution using radial base functions. This solution can not however be considered as a live display solution as some pre-processing must be applied offline to the participating media to be able to calculate projection coefficients representing the media that will be used for image synthesis live calculations.

With the emergence of interactive simulation games and applications, notably in three dimensions (3D), the need is being felt for live simulation methods offering a realistic display of heterogeneous participating media.

3. SUMMARY OF THE INVENTION

The purpose of the invention is to overcome at least one of these disadvantages of the prior art.

More specifically, the purpose of the invention is to optimise the required calculation time and/or calculation power required to compose a realistic live display of the scattering of light in a heterogeneous participating media.

The invention relates to a method for estimating the quantity of light scattered by a heterogeneous participating media, the method comprising steps for:

estimation of first projection coefficients in an orthonormal basis of spherical functions, the first projection coefficients being representative of the reduction of light intensity in a point of the media, the estimation of first projection coefficients being carried out for each point of the first set of points of the media, and estimation of the quantity of light scattered by the media, according to at least one scattering direction of the light, using first estimated projection coefficients.

According to a particular characteristic, each of the first projection coefficients is estimated using light intensity reduction values estimated along a plurality of light emission particular directions.

Advantageously, the estimation of light intensity reduction values is carried out via sampling of said light emission particular directions.

According to a specific characteristic, the method comprises a step of estimation of second projection coefficients in an orthonormal basis of spherical functions, the second projection coefficients being representative of incident light for a set of points of said light environment.

Advantageously, the method comprises a step of estimation of third projection coefficients in an orthonormal basis of spherical functions, the third projection coefficients being representative of the phase function for a second set of points of said media.

According to a particular characteristic, the estimation of the quantity of light scattered by the media is carried out by discretization of the media along the at least one scattering direction.

According to another characteristic, the estimation of the quantity of light scattered by the media is carried out using the ray sampling method.

Advantageously, the first projection coefficients are stored in a table of a memory associated with at least one graphics processor.

4. LIST OF FIGURES

The invention will be better understood, and other specific features and advantages will emerge upon reading the following description, the description making reference to the annexed drawings wherein.

5. DETAILED DESCRIPTION OF EMBODIMENTS OF THE INVENTION.

Figure 1:
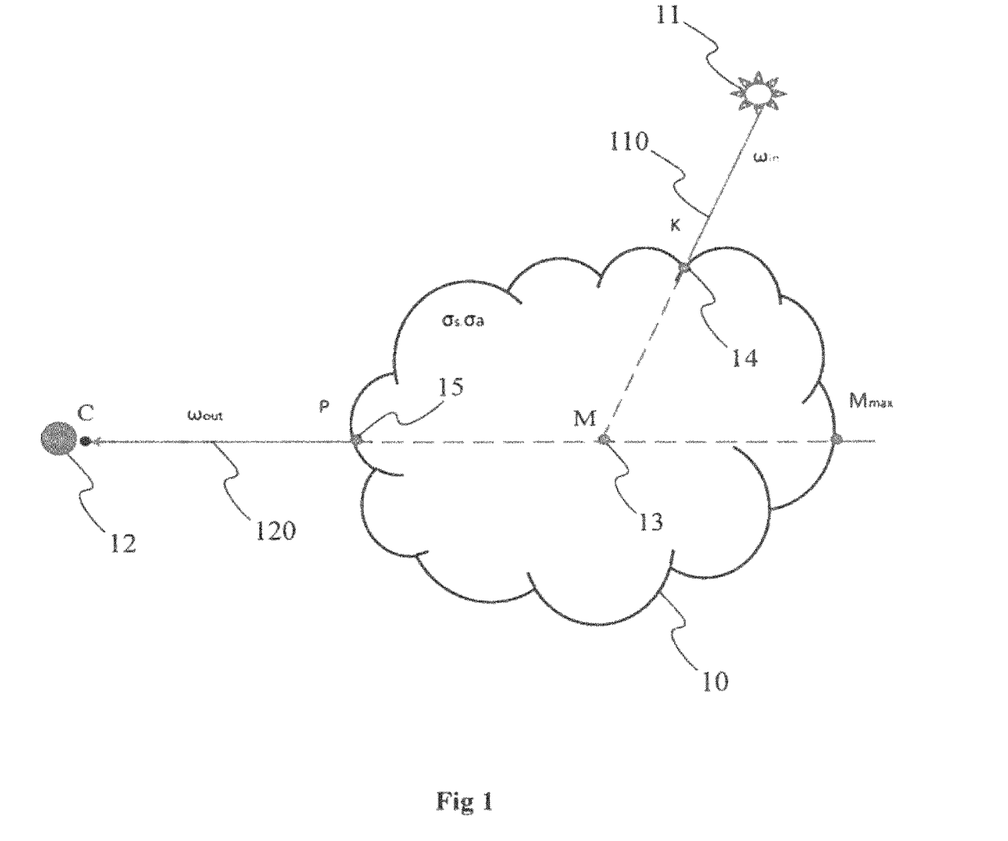
FIG. 1 diagrammatically shows a heterogeneous participating media scattering light, according to a particular embodiment of the invention.

FIG. 1 shows a heterogeneous participating media 10, for example a cloud. A participating media is a media, composed of a multitude of particles in suspension that absorbs, emits and/or diffuses light. In its simplest form, a participating media absorbs only light, for example the light received from a light source 11 such as the sun for example. This means that the light passing across the media 10 is attenuated, the attenuation depending of the density of the media. The media being heterogeneous, that is to say that the physical characteristics of the media, such as the density of particles composing it for example, vary from one point to another in the media. As the participating media is composed of small particles that interact with the light, the incident light, that is to say received from the light source 11 according to one direction $\omega_{in}$, 110 is not only absorbed but it is also scattered. In an isotropic scattering participating media, the light is scattered uniformly in all directions. In an anisotropic scattering participating media, such as the cloud 10 shown in FIG. 1, the light scattering depends on the angle between the incidence direction $\omega_{in}$, 110 and the scattering direction $\omega_{out}$, 120 of the light. The quantity of light scattered at a point M 13 of the media 10 in the scattering direction $\omega_{out}$, 120 is calculated by the following equation:

$$Q(M, \omega_{out}) = D(M).\sigma_s.p(M, \omega_{out}, \omega_{in}).L_{ri}(M, \omega_{in}) \quad \text{Equation 1}$$

The quantity of light scattered by a point M 13 of the media attaining the eye of the spectator 12 situated at a point C of space in the direction $\omega_{out}$, 120, that is to say the quantity of light scattered by the point M is attenuated by the media 10 on the trajectory M-P, the point P being situated at the intersection of the media 10 and the direction $\omega_{out}$, in the direction of the spectator 12, is then:

$$L_p(M, \omega_{out}) = Q(M, \omega_{out}).\exp^{\int_P^M -D(s)\sigma_t ds} \quad \text{Equation 2}$$

wherein:
- $\sigma_s$, is the scattering coefficient of the media,
- $\sigma_a$, is the absorption coefficient of the media,
- $\sigma_t = \sigma_s + \sigma_a$, is the extinction coefficient of the media,
- D(M) is the density of the media at a given point, the density varying from one point to another as the media 10 is heterogeneous,
- P(M, $\omega_{out}$, $\omega_{in}$) is the phase function describing how the light coming from the incidence direction $\omega_{in}$, is scattered in the scattering direction $\omega_{out}$, at the point M,
- $L_{ri}$(M, $\omega_{in}$) is the reduced light intensity at the point M coming from the incidence direction $\omega_{in}$, 110 and represents the quantity of Incident light arriving at the point M after attenuation due to the trajectory of the light in the media 10 on the segment K-M, K being the intersection point between the media 10 and the incidence ray $\omega_{in}$, 110, and its value is:

$$\exp^{\int_M^K -D(s)\sigma_s ds} \quad \text{Equation 3}$$

$\exp^{\int_P^M -D(s)\sigma_t ds}$, represents the attenuation of scattered light due to the absorption and scattering along the path from P 15 to M 13.

Equation 2, enables the quantity of light scattered by a point M and attaining the eye of a spectator 12 situated on the direction $\omega_{out}$, to be calculated. To calculate the quantity of light received by a spectator looking in the direction $\omega_{out}$, the sum of ail the contributions of the set of points of the media situated on the axis $\omega_{out}$, must be calculated, that is to say the points situated on the segment P-$M_{max}$, P and $M_{max}$, being the two intersection points between the media 10 and the direction $\omega_{out}$, 120. This total scattered light arriving at P 15 from the direction $\omega_{out}$, 120 due to simple scattering is then:

$$L(P, \omega_{out}) = \int_P^{M_{max}} L_p(M, \omega_{out}) dM \quad \text{Equation 4}$$

It is considered here that the light covering the trajectory C-P is not attenuated, the light not being attenuated outside the media 10.

This total scattered light is obtained by integration of contributions from all the points situated between P and $M_{max}$, on a ray having $\omega_{out}$, as direction. Such an integral equation cannot be resolved analytically in general and even less so for a live estimation of the quantity of light scattered. The integral is evaluated digitally using the method known as ray-marching. In this method, the integration domain is discretized into a multitude of intervals of size $\delta_M$, and the following equation is obtained:

$$L(P, \omega_{out}) \approx \Sigma_P^{Mmax} L_p(M, \omega_{out}) \delta_M \quad \text{Equation 5}$$

Advantageously, the heterogeneous participating media 10 is a three-dimensional element, shown in two dimensions on FIG. 1 for reasons of clarity.

According to a variant, the media 10 is lit by a plurality of light sources, for example 1000, 100,000, or 1,000,000, light sources.

Figure 2A:
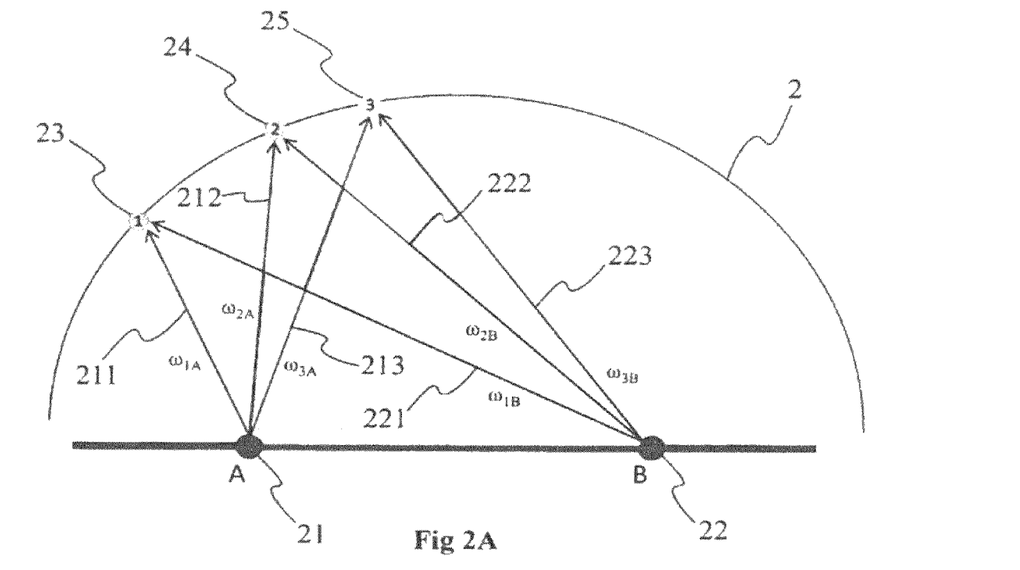
FIGS. 2A and 2B show a light environment comprising several light sources, according to a particular embodiment of the invention, FIG. 3 diagrammatically shows a method for estimation of the quantity of light scattered by a media of FIG. 1, lit by a light environment of FIGS. 2A and 2B, according to a particular embodiment of the invention, FIG. 4 diagrammatically shows a method for estimation of projection coefficients at each point of a set of points of the media of FIG. 1, according to a particular embodiment of the invention.
Figure 2B:
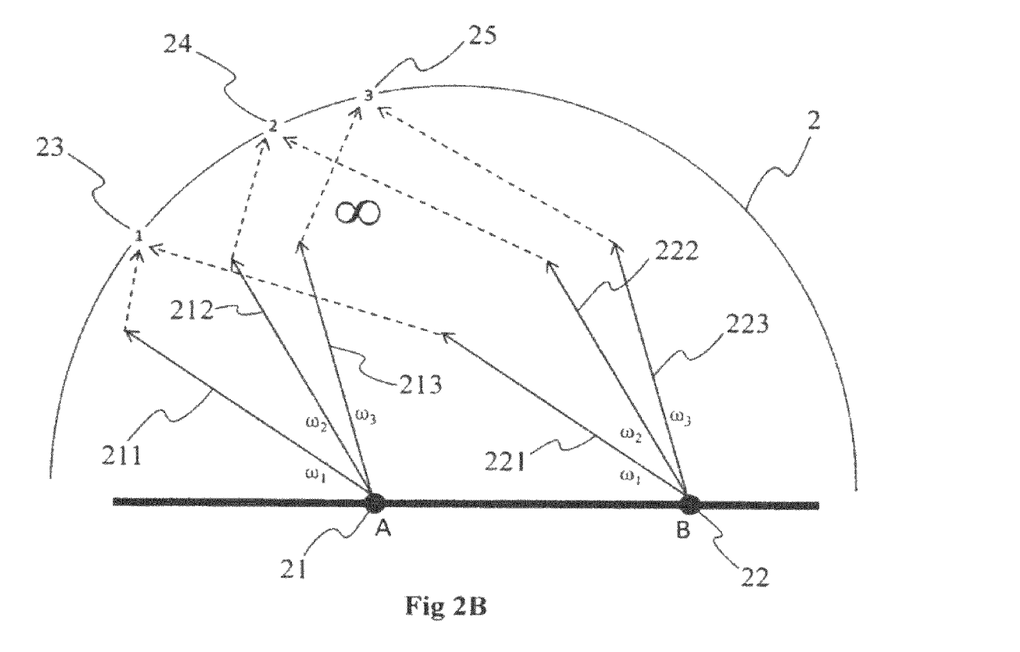

FIGS. 2A and 2B show a light environment 2 comprising several light sources 23, 24 and 25. Identical references are used for identical elements on FIGS. 2A and 2B. FIG. 2A shows more specifically two points A 21 and B 22 lit by three light sources 23, 24 and 25. The point A 21 is lit by the first light source 23 according to a direction $\omega_{1A}$ 211, by the second light source 24 according to a direction $W_{2A}$, 212 and by the third light source 25 according to a direction $\omega_{3A}$, 213. The point B 22 is lit by the first light source 23 according to a direction $\omega_{1B}$, 221, by the second light source 24 according to a direction $\omega_{2B}$, 222 and by the third light source 25 according to a direction $\omega_{3B}$, 223. The problem posed by such a complex light environment, as it has several light sources, is that it is very costly in terms of calculation for an estimation of incident light in a media because the direction of the light between a source and a point of the media is different for each point of the media. In fact, the direction taken by the light emitted from the first source 23 is different for A and for B, the direction taken by the light emitted by the second source 24 is different for A and for B and the direction taken by the light emitted by the third source 25 is different for A and for B. To resolve this problem, the estimation of the light coming from several distant light sources is carried out using the "environment mapping" method according to a particular embodiment of the invention, as shown in FIG. 2B. Rather than considering an exact direction of the light between the points A and B on one hand and the light sources 23, 24, 25 on the other hand (as shown in FIG. 2A), the environment mapping method considers that all the light sources 23, 24 et 25 of the environment 2 are situated at optical infinity with respect to the points A and B. It is thus possible to consider that the directions taken by the light emitted by a light source 23, 24 or 25 are identical for either of points A and B of the media considered. The parallax effect due to the distance separating the points A and B is thus negligible. The direction $\omega_{1A}$, 211 connecting the point A to the first light source 23 is considered as being identical to the direction $\omega_{1B}$, 221 connecting the point B to the first light source 23. Likewise, the direction $\omega_{2A}$, 212 connecting the point A to the second light source 24 is considered as being identical to the direction $\omega_{2B}$, 222 connecting the point B to the second light source 24 and the direction $\omega_{3A}$, 213 connecting the point A to the third light source 25 is considered as being identical to the direction $\omega_{36}$, 223 connecting the point B to the third light source 23.

According to a variant, the light environment comprises two or more light sources, for example 1000, 100,000, or 1,000,000, light sources.

Figure 3:
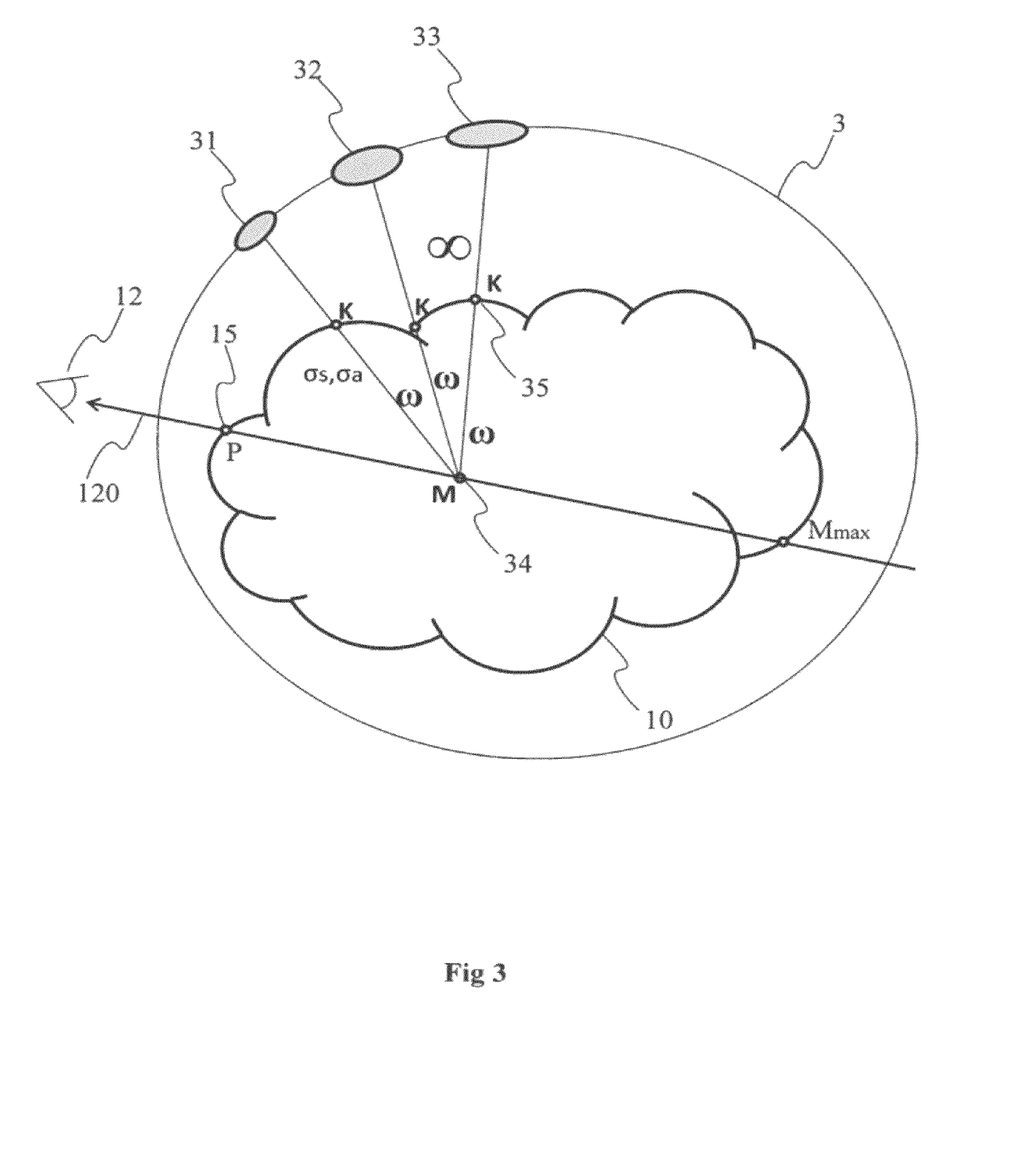

FIG. 3 shows a method for estimation of the quantity of light scattered by a media 10, the light being from a light environment 3 comprising several light sources 31, 32 and 33, according to a particular embodiment of the invention. As has been described with respect to FIG. 1, the scattered light at a point M 13 by the media 10 is a composition of the attenuation of light received by the media 10 from a light source 11 (or a light environment 3) and the scattering of this quantity of attenuated light received by the media 10. Initially, with respect to FIG. 3, the term of equation 1 representative of the attenuation of the light received from the light environment 3 in the media 10 is estimated. To do this, a sphere $\Omega$ surrounding the point M 34 is sampled. For each direction $\omega$ from the sphere $\Omega$ of centre M, the attenuation of the light along a path comprised between M and the exterior of the media is estimated using the following equation, equivalent to equation 3:

$$R(M,,\omega) = \exp^{\int_M^{K(\omega)} D(s)\sigma_t ds} \qquad \text{Equation 6}$$

where $R(M, \omega)$ is the attenuation of the light intensity at the point M 13 according to a direction $\omega$ and represents the quantity of incident light arriving at the point M after attenuation, D(s) is the density of the media, $\sigma_t$, is the extinction coefficient of the media, corresponding to the sum of the scattering coefficient of the media $a_s$, and the absorption coefficient of the media $\sigma_s$, ($\sigma_t = \sigma_s + \sigma_a$).

K 35 is the intersection point between the media 10 and the exterior of the media 10 following a direction $\omega$ leaving the point M.

Equation 6, provides the light attenuation at a point for a given direction $\omega$. To estimate the attenuation of light at the point M according to a direction $\omega$, the integration domain situated on the incidence direction $\omega$ is discretized into a series of intervals of size $\delta_s$, the density varying from one interval to another as the media 10 is heterogeneous. By applying the ray-marching method, a value of light attenuation at the point M is obtained according to the direction $\omega$. This value is recorded in a table of a memory associated with a GPU (Graphical Processing Unit). This operation of estimation of the light attenuation at the point M 34 is reiterated for each direction $\omega$ of the sphere $\Omega$ of centre M sampled in a set comprising N directions $\omega$ going from the point M, N being any natural positive integer. These values representative of the light attenuation at the point M according to a particular direction $\omega$ are stored in the memory table associated with the GPU.

Each function of the functional space can be written as a linear combination of base functions, a base function being an element of a base for a functional space. Using an orthonormal basis of spherical functions, it is possible to represent the light attenuation function at the point M by:

$$R(M) \approx \sum_{j=1}^{Nc} Cr_j(M) B_j(M) \qquad \text{Equation 7}$$

where R(M) is the light attenuation function at the point M, $Cr_j(M)$ is the $j^{ot}$, projection coefficient (on a total of Nc coefficients) of the base function $B_j(M)$ and where $Cr_j(M)$ is defined by the integral on the sphere $\Omega$, that is to say:

$$Cr_j(M) = \int_\Omega R(M, \omega) B_j(\omega) d\omega \qquad \text{Equation 8}$$

The set Nc of base function projection coefficients thus calculated is stored in a memory table of the GPU. These coefficients are representative of the attenuation of the light emitted by a light environment comprising several sources of light, due to the simple scattering of light from any direction for a particular given point M of the media 10.

Advantageously, the operations described above are reiterated for a set of points M of the media 10. For each point of the set of points, projection coefficients representative of the light attenuation according to all the directions are thus calculated and recorded in the tables called attenuation records. The greater the number of points M for which the projection coefficients are calculated the more the representation of the light attenuation due to simple scattering in the media 10 is accurate.

Likewise, the phase function of the media 10 can be represented using an orthonormal basis of spherical functions. It is considered that the phase function of the media 10 is the same at any point of the media 10. By projection the phase function $p(\omega_{out}, \omega_{in})$ into a set Nc of projection coefficients $Cp_j$, (called third projection coefficients) of a base of spherical functions B, the following is obtained:

$$Cp_j(\omega_{out}) = \int_\Omega p(\omega_{out}, \omega_{in}) B(\omega_{in}) d\omega_{in} \qquad \text{Equation 9}$$

This projection is carried out for a set N of directions $\omega$ going from the point M on a sphere $\Omega$. The projection coefficients representative of the phase function of the media are stored in a table of the memory associated with a GPU. According to a variant, the phase function varies from one point to another and the projection coefficients are calculated for a set of points representative of the media 10.

In an analogous manner, the function describing the environment mapping 3 representative of the incident light in the media 10 is represented using the orthonormal basis of spherical functions. By projecting the function representative of the environment mapping 3 into a set No of projection coefficients $Cl_j$, (called second projection coefficients) of a base of spherical functions B, the following is obtained:

$$Cl(\omega_{in}) = \int_\Omega L_i(\omega_{in}) B(\omega_{in}) d\omega_{in} \qquad \text{Equation 10}$$

where $Ll(\omega_{in})$ is the function of incident light according to an incidence direction $\omega_{in}$.

Advantageously, the light attenuation function, the phase function and the incident light function are represented in a single and same orthonormal basis of spherical functions.

As has been described with regard to FIG. 1, equation 1 describes the quantity of light scattered at a point M 13 of the media 10 in the scattering direction $\omega_{out}$, 120 for a light environment comprising a single source of light 11. Starting with this equation and adapting it for a light environment 3 comprising a plurality of light sources and described via an incident light function, the following simple scattering equation is obtained describing the light transmitted by the media 10 at a point M according to the direction $\omega_{out}$:

$$Q(M, \omega_{out}) = \int_\Omega \sigma_s(M) \cdot p(M, \omega_{out}, \omega_{in}) R(M, \omega_{in}) d\omega_{in} \qquad \text{Equation 11}$$

The functions R, $L_j$, and p were projected into a set of projection coefficients of spherical base functions, respectively into a set of first coefficients, into a set of second coefficients s and into a set of third coefficients. The projection coefficients are respectively noted $\{Cr_j\}_{j=0 \ldots n}$, $\{Cl_j\}_{j=0 \ldots N}$, and $\{Cp_j\}_{j=0 \ldots N}$. The projection coefficients describing the light attenuation function having been estimated for a set of points of the media 10 and not for all of the points of the media M, the projection coefficients for R for the points for which they were not estimated via equation 8, are calculated by interpolation as described in FIG. 4 To obtain the first projection coefficients of the attenuation function at the point M 44 situated on the observation direction 46 of a spectator 45, an interpolation of first projection coefficients of the function R estimated for the four points situated in the neighbouring area of M 44, namely the points 441, 442, 443 and 444, is carried out.

Figure 4:
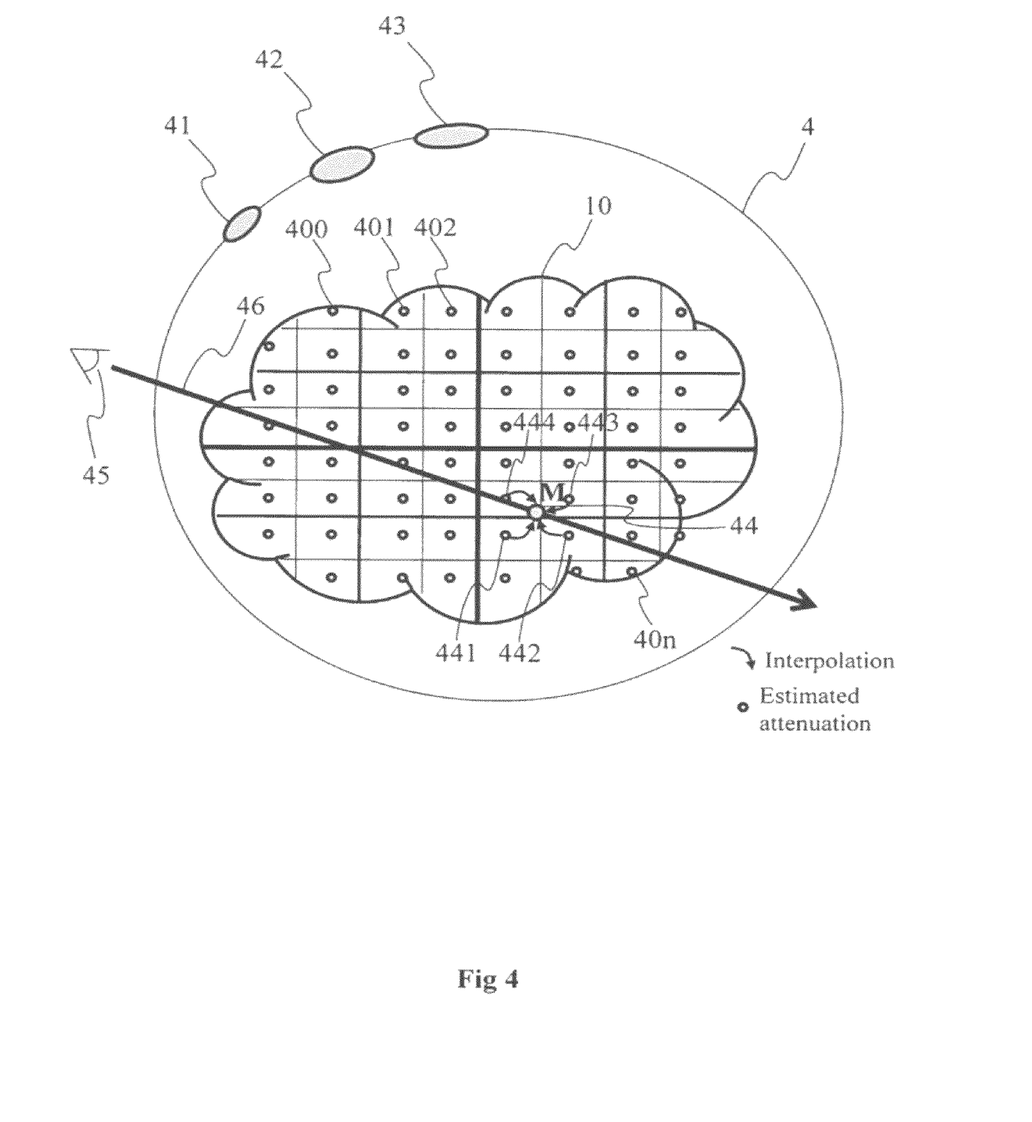

Using the first projection coefficients representative of the attenuation of light in the media, the light coming from the light environment (estimated via equation 8, described in respect of FIG. 2 and by interpolation as described with respect to FIG. 4), second projection coefficients representative of the incident light and third projection coefficients representative of the phase function of the media 10, it is possible to estimate the global attenuation of the light at a point M as it is received by a spectator 36 analytically, the resources in terms of calculating power required being very much less with respect to those required for an analytic resolution of integral form equations. To calculate the triple product of projected functions, the tensor product well known to those skilled in the art is used and using equations 2, 8, and 11, it is then possible to estimate the quantity of light emitted by a point M 13 of the media and received by a spectator 12 looking in the direction $\omega_{out}$. The following is thus obtained:

$$Q(M, \omega_{out}) \approx \Sigma C p_i(\Sigma_j, \Sigma_k, \Gamma_{jki} Cl_j Cr_k) \qquad \text{Equation 12}$$

where $\Gamma_{jki}$, represents the tensor product, that is calculated according to $$\Gamma_{jki} = \int_\Omega B_j(\omega) B_k(\omega) B_i(\omega) d\omega \qquad \text{Equation 13}$$

Equation 12, represents the quantity of light emitted by a point M and received by a spectator. To obtain the total quantity of light received by a spectator situated at a point C looking in the direction $\omega_{out}$, 120, it suffices to add the sum of quantities of elementary light emitted by the set of points $M_j$ going from P to $M_{max}$, The following equation is obtained:

$$Q(C, \omega_{out}) \approx \Sigma_p^{Mmax} L_p(M, \omega_{out}) \delta M \qquad \text{Equation 14}$$

To obtain the total quantity of light scattered by the media 10 and received by the spectator, the estimations described above are reiterated for all directions leaving the user and crossing the media 10. The sum of light quantities received by the spectator according to each observation direction provides the quantity of light received from the media 10 by the spectator 12.

Figure 5:
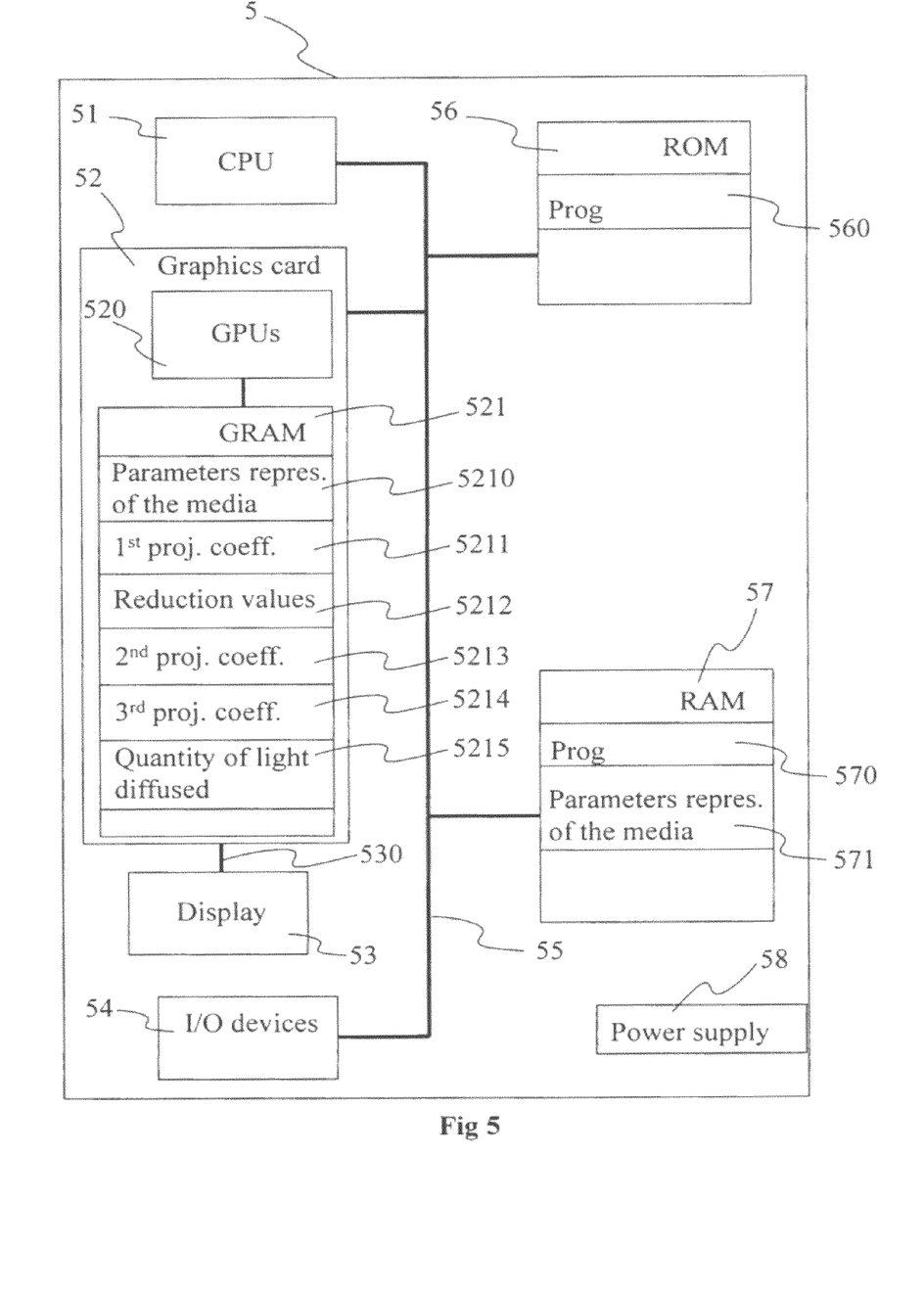
FIG. 5 shows a device implementing a method for estimation of the quantity of light scattered, according to a particular embodiment of the invention.

FIG. 5 diagrammatically shows a hardware embodiment of a device 5 adapted for the estimation of the quantity of light scattered by a heterogeneous participating media 10 and at the creation of display signals of one or several images. The device 5 corresponding for example to a personal computer PC, a laptop or a games console.

The device 5 comprises the following elements, connected to each other by a bus 45 of addresses and data that also transports a clock signal:
  a microprocessor 51 (or CPU),
  a graphics card 52 comprising:
    several Graphicole Processor Units (or GPUs) 520,
    a Graphical Random Access Memory (GRAM) 521,
  a non-volatile memory of ROM (Read Only Memory) type 56,
  a Random Access Memory or RAM 57,
  one or several I/O (Input/Output) devices 54 such as for example a keyboard, a mouse, a webcam, and
  a power source 58.

The device 5 also comprises a display device 53 of display screen type directly connected to the graphics card 52 to display notably the display of synthesized images calculated and composed in the graphics card, for example live. The use of a dedicated bus to connect the display device 53 to the graphics card 52 offers the advantage of having much greater data transmission bitrates and thus reducing the latency time for the displaying of images composed by the graphics card. According to a variant, a display device is external to the device 5 and is connected to the device 5 by a cable transmitting the display signals. The device 5, for example the graphics card 52, comprises a means for transmission or connection (not shown in FIG. 5) adapted to transmit a display signal to an external display means such as for example an LCD or plasma screen or a video-projector.

It is noted that the word "register" used in the description of memories 52, 56 and 57 designates in each of the memories mentioned, both a memory zone of low capacity (some binary data) as well as a memory zone of large capacity (enabling a whole program to be stored or ail or part of the data representative of data calculated or to be displayed).

When switched-on, the microprocessor 51 loads and executes the instructions of the program contained in the RAM 57.

The random access memory 57 notably comprises:
  in a register 530, the operating program of the microprocessor 51 responsible for switching on the device 5,
  parameters 571 representative of the heterogeneous participating media 10 (for example parameters of density, of light absorption coefficients, of light scattering coefficients).

The algorithms implementing the steps of the method specific to the invention and described hereafter are stored in the memory GRAM 57 of the graphics card 52 associated with the device 5 implementing these steps. When switched on and once the parameters 570 representative of the environment are loaded into the RAM 47, the graphic processors 520 of the graphics card 52 load these parameters into the GRAM 521 and execute the instructions of these algorithms in the form of microprograms of "shader" type using HLSL (High Level Shader Language) language or GLSL (OpenGL Shading Language) for example.

The random access memory GRAM 521 notably comprises:
  in a register 5210, the parameters representative of the media 10,
  first projection coefficients 5211 representative of the reduced light intensity at each point of the media 10,
  light intensity reduction values 5212 for each point of the media 10,
  second projection coefficients 5213 representative of incident light at each point of the media 10,
  third projection coefficients 5214 representative of the phase function at each point of the media 10, and
  values 5215 representative of the quantity of light scattered by the media 10 according to one or several observation directions.

According to a variant, a part of the RAM 57 is assigned by the CPU 51 for storage of the coefficients 5211, 5213 and 5214 and values 5212 W to 5215 if the memory storage space available in GRAM 521 is insufficient. This variant however causes greater latency time in the composition of an image comprising a representation of the media 10 composed from microprograms contained in the GPUs as the data must be transmitted from the graphics card to the random access memory 57 passing by the bus 55 for which the transmission capacities are generally inferior to those available in the graphics card for transmission of data from the GPUs to the GRAM and vice-versa.

According to another variant, the power supply 58 is external to the device 5.

Figure 6:
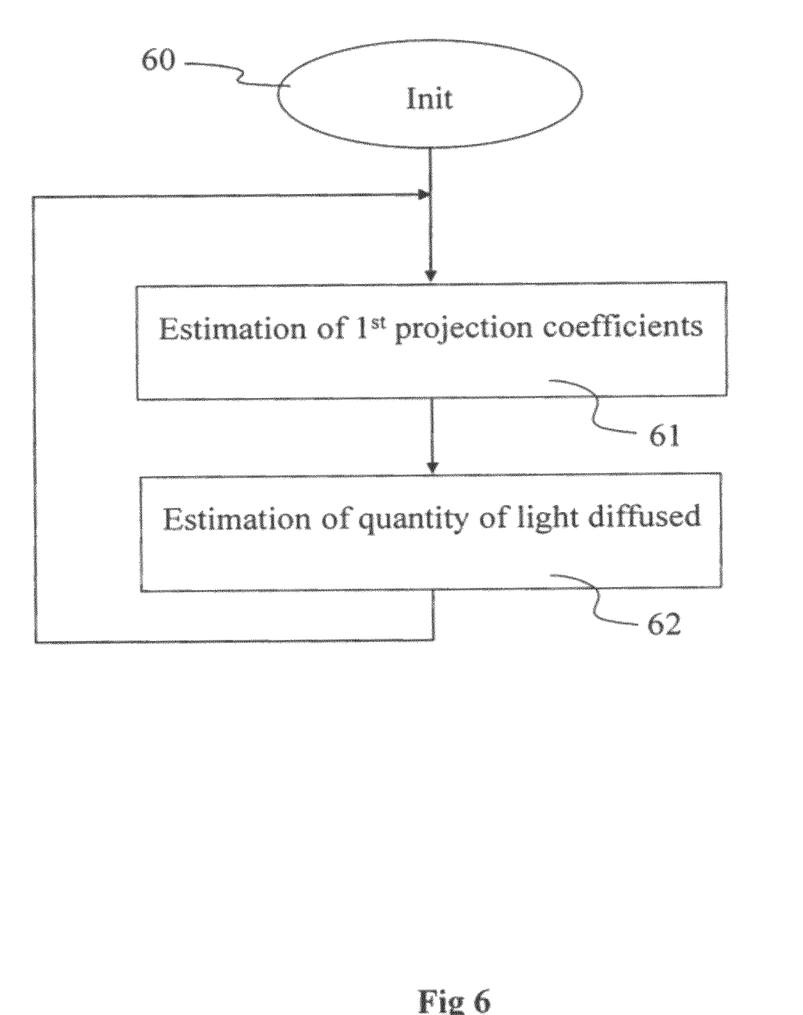
FIGS. 6 and 7 show a method for estimation of the quantity of light scattered, according to two particular embodiments of the invention.

FIG. 6 shows a method for estimation of the quantity of light scattered by a heterogeneous participating media implemented in a device 5, according to a first non-restrictive particularly advantageous embodiment of the invention.

During an initialisation step 60, the different parameters of the device 5 are updated. In particular, the parameters representative of the heterogeneous participating media 10 are initialised in any way.

Then, during a step 61, first projection coefficients of a base function in an orthonormal basis of spherical functions are estimated, these first projection coefficients being representative of the reduction in light intensity at a given point of the heterogeneous participating media 10. To do this, a plurality of values representative of the reduction in light intensity are calculated for the given point M 34 of the media 10 for a plurality of given incidence directions. Each value representative of the reduction in light intensity corresponds to a given incidence direction among a plurality of incidence directions. For each incidence direction of the plurality of incidence directions going from the light environment to join the point M 34, the value representative of the reduction in light intensity at the point M 34 is calculated using any sampling method known to those skilled in the art, advantageously, using the method known as the ray-marching algorithm method. The plurality of incidence directions $\omega$ (or $\omega_{in}$) for which are calculated values representative of the reduction of light intensity at the point M form a sphere $\Omega$ having as centre M. The number of directions $\omega$ for which are calculated the values representative of the reduction of light intensity at the point M is chosen in a way to find the best compromise between the calculating power required for the calculation of these values and the precision of the estimation of the reduction in light intensity at the point M desired by the user of the device 5. Choosing a number of directions $\omega$ means sampling the sphere $\Omega$ having as centre M.

Advantageously, step 61 is reiterated for each point of a first set of points (for example 50, 100, or 1000, points) representative of the media 10. First projection coefficients representative of the reduction in light intensity at each of the points of the first set of points are thus obtained. In other words, a set of first projection coefficients corresponds to a point of the media and there are as many sets of first projection coefficients calculated as there are points in the first set of points representative of the media 10. To obtain the first projection coefficients for the points of the media for which these first coefficients have not been calculated, an interpolation of first calculated projection coefficients is used.

Then, during a step 62, the quantity of light scattered by the media 10 according to an emission direction 120 is estimated using the first projection coefficients estimated previously. To do this the line segment corresponding to the intersection of the emission direction 120 with the media 120, that is to say the segment $[PM_{max}]$ is spatially discretized into a multitude of points or elementary parts representative of this segment. For each point of this segment (respectively each elementary part), equation 12, is applied using the first projection coefficients previously estimated. According to a variant, the ray-marching method is implemented to estimate the reduction of light intensity between a point of the segment considered and the point P 15 situated on the periphery of the media 10 in the emission direction 120. The use of first projection coefficients representative of the reduction in light intensity at points of the media enables the calculations to be implemented to be simplified while providing a realistic estimation of the reduction of light intensity in a heterogeneous media. No pre-calculation is then required to carry out the display of the scattering of light in a heterogeneous participating media, authorising the live display of such media in interactive applications of video game type for example in which the user is led to move virtually in a space comprising one or several heterogeneous participating media.

Advantageously, the quantity of light scattered by the media 10 is estimated for several emission directions. By adding the sum of these quantities of light estimated for a plurality of emission directions, a total quantity of light scattered by the media 10 and perceived by a spectator observing the media 10 is obtained.

Steps 61 and 62 are advantageously reiterated as a spectator 12 moves around the media 10, the image forming the display of the media 10 being recomposed for each elementary displacement of the spectator 12 around the media 10.

Figure 7:
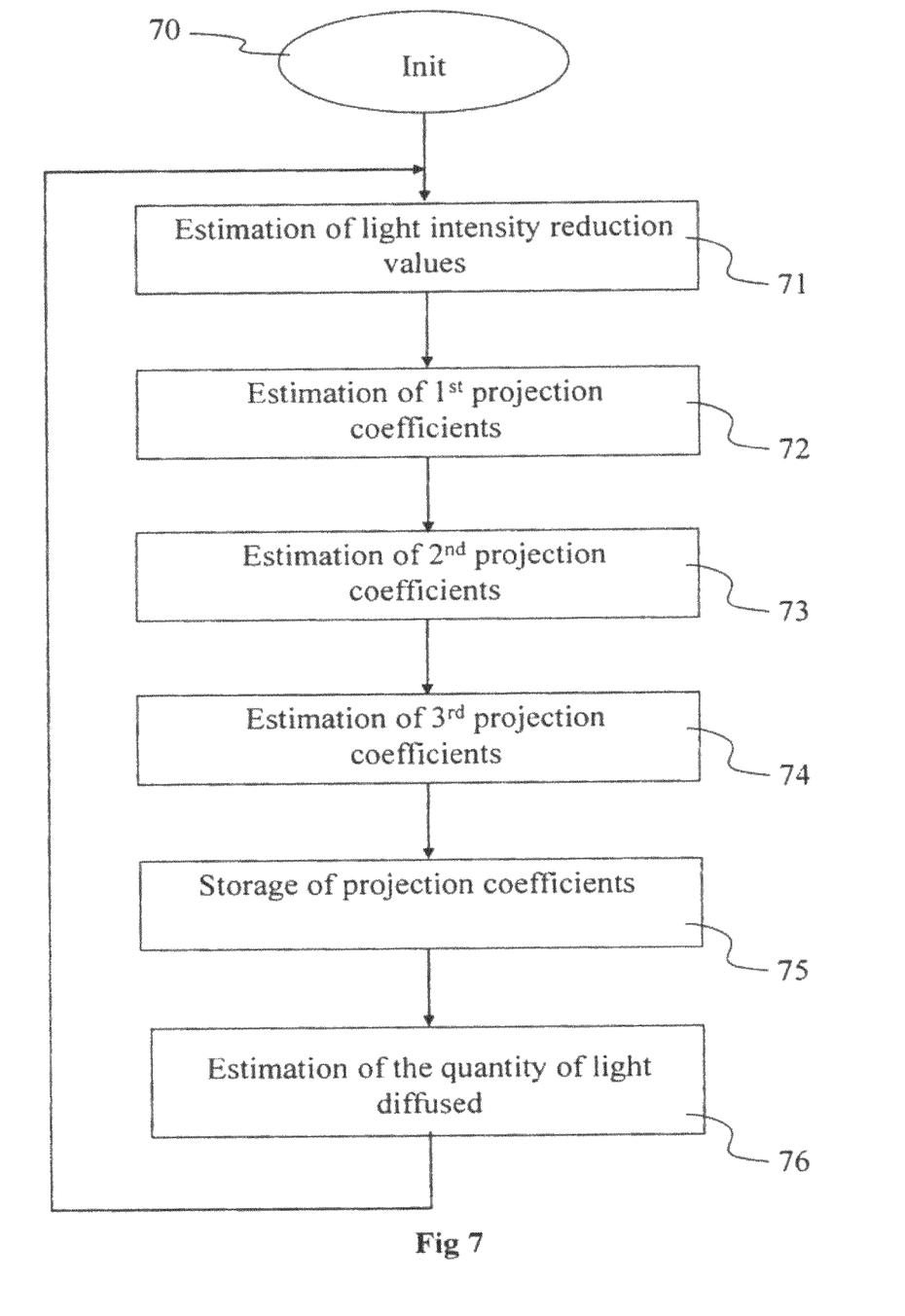

FIG. 7 shows a method for estimation of the quantity of light scattered by a heterogeneous participating media implemented in a device 5, according to a second non-restrictive particularly advantageous embodiment of the invention.

During an initialisation step 70, the different parameters of the device 5 are updated. In particular, the parameters representative of the heterogeneous participating media 10 are initialised in any way.

Then, during steps 71 and 72, values of reduction in light intensity are estimated in a plurality of points of the media 10 then first projection coefficients are estimated in the same way as described with respect to step 61 of FIG. 6. Steps 71 and 72 are thus not described again here.

Then during a step 73, second projection coefficients representative of incident light are estimated for a set of points of the light environment 3, the points of the set being representative of the light environment. To do this, the function describing the environment mapping 3 (called incident light function) representative of incident light in the media 10 is represented using the orthonormal basis of spherical functions having served to represent the light attenuation function. The function representative of the environment mapping 3 is thus projected into a set of second projection coefficients of a base of spherical functions. Advantageously, these second coefficients are stored in a table of a memory associated with one or several GPUs of the graphics card of the device 5. The second projection coefficients are advantageously identical in any point of the light environment. According to a variant, the second projection coefficients vary, from one point to another or from one set of points to another belonging to the light environment.

Then during a step 74, third projection coefficients representative of the phase function of the media 10 are estimated for a second set of points of the media 10, the points of the set being representative of the light environment. To do this, the function describing the phase function of the media 10 is represented using the orthonormal basis of spherical functions having served to represent the light attenuation function and the incident light function. The phase function is thus projected into a set of third projection coefficients of a spherical functions base. Advantageously, these third coefficients are stored in a table of a memory associated with one or several GPUs of the graphics card of the device 5. The third projection coefficients are advantageously identical in any point of the media. According to a variant, the third projection coefficients vary from one point to another or from one set of points to another belonging to the media 10.

According to a variant, the steps 73 and 74 are executed before steps 71 and 72. According to another variant, the steps 72, 73 and 74 are executed simultaneously, for example in parallel on dedicated GPUs.

Then during a step 75, the first projection coefficients previously estimated are recorded and stored in a structure of data composed of tables recorded in a memory associated with the GPUs. These recordings are called attenuation recordings. The attenuation recording tables advantageously comprise the set of first projection coefficients of points of the media 10, these first coefficients having been calculated from equation 8 or by interpolation from first coefficients calculated via equation 8. There is a set of first projection coefficients per point of the media 10 or according to a variant for a set of points representative of the media 10. Such a storage of first projection coefficients offer the advantage of accelerating the calculations for estimating the quantity of light scattered by the media 10 and perceived by a spectator, the first projection coefficients representative of the reduction of incident light intensity being available at any time and immediately for use in equations 12, and 13. Likewise, the recording of second projection coefficients and third projection coefficients in dedicated tables accelerates the calculations, particularly when the second and third coefficients vary from one point to another (respectively the light environment 3 and the media 10).

Finally, during a step 76, the quantity of light scattered is estimated in the same way as that described in reference to step 62 of FIG. 5.

Naturally, the invention is not limited to the embodiments previously described.

In particular, the invention is not limited to a method for estimation of the quantity of light scattered by a heterogeneous participating media but also extends to any device implementing this method and notably any devices comprising at least one GPU. The implementation of equations described with respect to FIGS. 1 to 4 for the estimation of first, second and third coefficients of projection, of reduction of light intensity, of the quantity of light scattered is also not limited to an implementation of shader type microprograms but also extends to an implementation in any program type, for example programs that can be executed in a CPU type microprocessor.

Advantageously, the base functions used for the estimation of projection coefficients are spherical harmonics of spherical wavelet type functions.

The use of the invention is not limited to a live utilisation but also extends to any other utilisation, for example for processing known as postproduction processing in a recording studio for the display of synthesis images for example. The implementation of the invention in postproduction offers the advantage of providing an excellent visual display in terms of realism notably while reducing the required calculation time.

The invention also relates to a method for composition of a video image, in two dimensions or in three dimensions, for which the quantity of light scattered by a heterogeneous participating media is calculated and the information representative of the light that results is used for the displaying of pixels of the image, each pixel corresponding to an observation direction according to an observation direction $\omega_{out}$. The calculated light value for displaying by each of the pixels of the image is re-calculated to adapt to the different viewpoints of the spectator.

The present invention can be used in video game applications for example, whether via programs that can be executed in a PC or portable type computer or in specialised game consoles producing and displaying images live. The device 5 described with respect to FIG. 5 is advantageously equipped with interaction means such as a keyboard and/or joystick, other modes for introduction of commands such as for example vocal recognition being also possible.

The invention claimed is:

1. Method for estimating the quantity of light scattered by a heterogeneous participating media, the light being emitted by a light environment comprising a plurality of light sources, wherein the method comprises steps for: selection of some points from said media to form a first set of points of said media, for each point of said first set, estimation of a plurality of light intensity reduction values along a plurality of particular light emission directions, For each point of said first set, estimation of first projection coefficients representative of light intensity reduction in said point by projection of said light intensity reduction values in an orthonormal basis of spherical functions, and estimation of the quantity of light scattered by said media, according to at least one scattering direction of the light, using said first estimated projection coefficients.

2. Method according to claim 1, wherein the estimation of said light intensity reduction values is carried out by sampling of said particular light emission directions.

3. Method according to claim 1, wherein it comprises a step of estimation of second projection coefficients in said orthonormal basis of spherical functions, said second projection coefficients being representative of the incident light for a set of points of said light environment.

4. Method according to claim 1, wherein it comprises a step of estimation of third projection coefficients in said orthonormal basis of spherical functions, said third projection coefficients being representative of the phase function for a second set of points of said media.

5. Method according to claim 1, wherein said estimation of the quantity of light scattered by said media is carried out by discretization of said media along the at least one scattering direction.

6. Method according to claim 1, wherein said estimation of the quantity of light scattered by said media is carried out using the ray-marching algorithm method.

7. Method according to claim 1, wherein said first projection coefficients are stored in a table of a memory associated with at least one graphical processor.

8. Device configured for estimating the quantity of light scattered by a heterogeneous participating media, the light being emitted by a light environment comprising a plurality of light sources, wherein the device comprises: a processing circuit for selecting some points from said media to form a first set of points of said media, a processing circuit for estimating a plurality of light intensity reduction values along a plurality of particular light emission directions for each point of said first set, a processing circuit for estimating, for each point of said first set, first projection coefficients representative of the light intensity reduction in said by projection of said light intensity reduction values in an orthonormal basis of spherical functions, and a processing circuit for estimating the quantity of light scattered by said media, according to at least one scattering direction of the light, using said first estimated projection coefficients.

9. Device according to claim 8, wherein it comprises a processing circuit for estimating second projection coefficients in said orthonormal basis of spherical functions, said second projection coefficients being representative of the incident light for a set of points of said light environment.

10. Device according to claim 8, wherein it comprises a processing circuit for estimating third projection coefficients in said orthonormal basis of spherical functions, said third projection coefficients being representative of the phase function for a second set of points of said media.

* * * * *